United States Patent [19]

Wolf

[11] 4,192,830

[45] Mar. 11, 1980

[54] HALOGENATED PHOSPHONITRILIC ESTERS

[75] Inventor: Rainer Wolf, Allschwil, Switzerland

[73] Assignee: Sandoz Ltd., Basel, Switzerland

[21] Appl. No.: 921,551

[22] Filed: Jul. 3, 1978

[30] Foreign Application Priority Data

Jul. 7, 1977 [CH] Switzerland ............... 8421/77
Jul. 7, 1977 [CH] Switzerland ............... 8422/77

[51] Int. Cl.$^2$ ............................................... C07F 9/02
[52] U.S. Cl. ............................. 260/973; 260/927 N
[58] Field of Search ...................... 260/927 N, 973

[56] References Cited

U.S. PATENT DOCUMENTS

| | | | |
|---|---|---|---|
| 2,192,921 | 3/1940 | Lipkin | 260/927 N |
| 2,586,312 | 2/1952 | Dishon et al. | 260/927 N |
| 2,681,295 | 6/1954 | Hamalainen | 260/927 N |
| 3,836,599 | 9/1974 | Franko-Filipasic et al. | 260/927 N |
| 3,836,608 | 9/1974 | Franko-Filipasic et al. | 260/927 N |
| 3,869,294 | 3/1975 | Lanier et al. | 260/927 N |
| 3,894,121 | 7/1975 | Wolf | 260/927 N |
| 3,894,876 | 7/1975 | Wolf | 260/927 N |
| 3,965,219 | 6/1976 | Ager | 260/973 |
| 3,974,242 | 8/1976 | Lanier et al. | 260/927 N |

*Primary Examiner*—Mary C. Lee
*Attorney, Agent, or Firm*—Gerald D. Sharkin; Richard E. Vila; Thomas C. Doyle

[57] ABSTRACT

Alkaline earth metal oxides are used as acid binding agents in the production of halogenated phosphonitrilic esters from phosphonitrilic halides and halogenated aliphatic alcohols and/or halogenated aliphatic diols. The products are useful as flameproofing agents for textiles, plastics and synthetic resins.

10 Claims, No Drawings

HALOGENATED PHOSPHONITRILIC ESTERS

The present invention relates to a process of production of phosphonitrilic esters.

In U.S. Pat. No. 3,894,121, there is described a process for producing certain halogenated phosphonitrilic esters comprising reacting one or more phosphonitrilic halides of formula II,

    II in which
q is an integer 3 to 12, and
Hal is fluorine, chlorine or bromine,
with one or more alcohols selected from the group consisting of those of formula III,

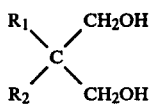    III and those of formula IV,

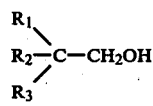    IV in which
each of $R_1$, $R_2$ and $R_3$, independently, is a halogenated lower alkyl radical,
preferably in a molar ratio of the one or more phosphonitrilic halides of formula II to the one or more alcohols selected from the group consisting of those of formula III and those of formula IV of 1:1 to 2q. The phosphonitrilic ester products are indicated to have the general formula I,

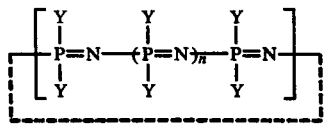    I in which
n is an integer 1 to 10,
and each
Y, independently, is a halogen atom, i.e. the same halogen, Hal, present in the appropriate starting phosphonitrilic halide of formula II, or a radical (a)

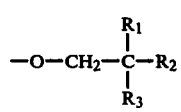    (a)

or a radical (b)

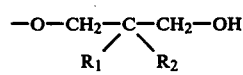    (b)

or forms, together with a second Y on the same or a different phosphorus atom, a divalent radical (c)

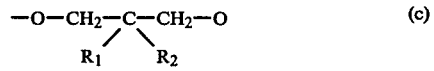    (c)

wherein each of
$R_1$, $R_2$ and $R_3$, independently is a halogenated lower alkyl radical,
at least one Y signifying other than a halogen atom.

The reaction is indicated in the patent to be preferably carried out in an inert organic solvent and in the presence of an acid binding agent. The suitable acid binding agents mentioned are hydroxides and carbonates of alkali metals and of alkaline earth metals, ammonium hydroxide and carbonate, quaternary ammonium hydroxides, tri-(lower alkyl)amines, pyridine, picoline and quinoline.

According to the present invention, there is provided a process, as defined above, for producing halogenated phosphonitrilic esters, the improvement in which consists of using an acid binding agent comprising one or more alkaline earth metal oxides.

Preferably the alkaline earth metal oxides used in the process of the present invention are selected from calcium oxide, magnesium oxide and barium oxide, of which calcium oxide and magnesium oxide are more preferred, and calcium oxide is most preferred. The acid binding agent may consist entirely of one or more alkaline earth metal oxides, but is preferably a mixture of one or more alkaline earth metal oxides and one or more alkali metal hydroxides. Preferred examples of the latter are sodium hydroxide, potassium hydroxide and lithium hydroxide, of which sodium hydroxide and potassium hydroxide are more preferred, and sodium hydroxide is most preferred. The proportion of the one or more alkali metal hydroxides in a mixture with one or more alkaline earth metal oxides is preferably 40–80%, more preferably 55–65% by weight of the total acid binding agent. Most preferably, the acid binding agent consists of a mixture of calcium oxide and sodium hydroxide, especially in a 40:60 weight ratio, or one not differing substantially therefrom.

The reaction is suitably carried out in an inert organic solvent, preferably one of these mentioned in U.S. Pat. No. 3,894,121. Most preferably, acetone is used as the solvent.

The phosphonitrilic halides of formula II are preferably the reaction products of ammonium halides and phosphorus pentahalides, as indicated in U.S. Pat. No. 3,894,121.

In the starting materials of formulae III and IV, the halogenated lower alkyl radicals signified by $R_1$, $R_2$ and $R_3$ are preferably halogenated ($C_{1-5}$)alkyl, more preferably monohalogenated methyl.

The halogen substituents are selected from fluorine, chlorine and bromine, of which chlorine and bromine are preferred. Thus, particularly preferred compounds of formulae III and IV for use in the process of the present invention are 2,2-bis-(chloromethyl)-propane-1,3-diol and 2,2-bis-(bromomethyl)-propane-1,3-diol; and 3-chloro-2,2-bis-(chloromethyl)-1-propanol and 3-bromo-2,2-bis-(bromomethyl)-1-propanol, respectively.

The molar proportion in which the compound or compounds of formula II is or are reacted with the compound or compounds of formula III and/or of formula IV is preferably 1:1 to 2q, more preferably 1:2q, respectively, and the temperature range in which the reaction is effected is generally 0° to 200° C., preferably 10° to 100° C., and most preferably 15° to 35° C.

When the acid binding agent consists entirely of one or more alkaline earth metal oxides, the amount of such binding agent used is preferably at least half the molar amount of hydroxyl groups present in the compound or compounds of formula III and/or IV, and more preferably from half the molar amount to a molar amount. When a mixed acid binding agent comprising one or more alkali metal hydroxides is used, the molar quantity of alkaline earth metal oxide used is preferably correspondingly reduced by the molar quantity of alkali metal hydroxide present.

On completion of the reaction, the product may be isolated in conventional manner. For example, the reaction mixture may be freed of the solvent by evaporation and the residue added to an aqueous acidic medium to cause precipitation of the product, which may then be separated, washed, e.g. in water, and dried.

As will be appreciated, the reaction between the compounds of formula II and III and/or IV will result in mixed products. While separation of at least the major constituents of any such mixed products may, in some cases, be possible, isolation of the various constituents is not generally necessary for producing useful final products, and indeed satisfactory results are obtained by the use of such mixed products.

The process of the present invention affords halogenated phosphonitrilic esters in suprisingly higher yields than the analogous processes in which other acid binding agents, e.g. those mentioned in U.S. Patent 3,894,121, are used instead of alkaline earth metal oxides.

The halogenated phosphonitrilic esters obtained by the process of the present invention are useful as flameproofing agents for textiles, plastics and synthetic resins, the application of the flameproofing agents to such substrates being described and exemplified in U.S. Pat. No. 3,894,121.

In the following Example, which illustrates the process of the present invention, the parts and percentages are by weight and the temperatures are in degrees Centigrade.

EXAMPLE

A mixture consisting 464 parts of an oligomeric phosphonitrilic chloride of approximate composition 60–70% $P_3N_3Cl_6$, 10–15% $P_4N_4Cl_8$ and the remainder predominantly a mixture of phosphonitrilic chlorides $P_xN_xCl_{2x}$, wherein x is an integer 5 to 12, 630 parts of acetone, 202 parts of calcium oxide and 1048 parts of a technical mixture containing 80–82% 2,2-bis(bromomethyl)propane-1,3-diol and 11–15% 3-bromo-2,2-bis(-bromomethyl)-1-propanol is cooled to 15° C., and 320 parts of sodium hydroxide pellets are added portionwise with the temperature of the mixture maintained at a maximum of 35°. The mixture is then stirred for 2 hours at 20° and for 24 hours at 35°. After the mixture has been cooled to room temperature, 1900 parts of isopropanol are added and the whole is concentrated by distillation until about 900 parts of isopropanol/acetone mixture have been distilled off. The concentrate is added to a mixture of 6000 parts of ice and 710 parts of concentrated hydrochloric acid, and the mixture is stirred for 30 minutes and then filtered. Washing of the resulting filter cake with water and subsequent drying affords a white solid which softens in the range 90° to 100° and is soluble in chloroform, acetone, tetrahydrofuran, dimethylformamide and dimethylsulphoxide. On analysis, the product is shown to have a 47.0% bromine content and a 1.7% chlorine content. The yield is approximately 1142 parts.

What is claimed is:

1. In a process for producing halogenated phosphonitrilic esters comprising reacting one or more phosphonitrilic halides of formula II, $$P_qN_qHal_{2q} \qquad \qquad II$$

in which
q is an integer 3 to 12, and
Hal is fluorine, chlorine or bromine,
with one or more alcohols selected from the group consisting of those of formula III,

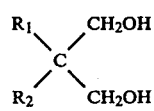

and those of formula IV,

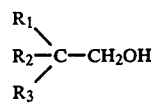

in which each of
$R_1$, $R_2$ and $R_3$, independently, is halogenated lower alkyl,
in the presence of an acid binding agent, the improvement wherein the acid binding agent comprises one or more alkaline earth metal oxides or a mixture of one or more alkaline earth metal oxides and up to 80% by weight of said mixture, of one or more alkali metal hydroxides, the total number of mols of said alkaline earth metal oxides and alkali metal hydroxides being equal to at least half the number of hydroxyl groups present in said alcohol(s).

2. A process according to claim 1, in which the alkaline earth metal oxide is calcium oxide, magnesium oxide or barium oxide or a mixture thereof.

3. A process according to claim 1, in which the acid binding agent consists of a mixture of one or more alkaline earth metal oxides and one or more alkali metal hydroxides.

4. A process according to claim 3, in which the acid binding agent consists of a mixture of calcium oxide and sodium hydroxide.

5. A process according to claim 3, in which the proportion of the one or more alkali metal hydroxides in the mixture with one or more alkaline earth metal oxides is 55 to 65% by weight of the total acid binding agent.

6. A process according to claim 1, which is carried out in an inert organic solvent, said solvent being acetone.

7. A process according to claim 1, in which the alcohols of formula III are 2,2-bis-(chloromethyl)-propane-1,3-diol and 2,2-bis-(bromomethyl)-propane-1,3-diol, and the alcohols of formula IV are 3-chloro-2,2-bis- (chloromethyl)-1-propanol and 3-bromo-2,2-bis-(bromomethyl)-1-propanol.

8. A process according to claim 2 wherein the alkali metal hydroxide is sodium hydroxide, potassium hydroxide or lithium hydroxide or a mixture thereof.

9. A process according to claim 1 wherein the mol ratio of phosphonitrilic halide to alcohol is in the range 1:1 to 1:2q.

10. A process according to claim 4 wherein the weight ratio of calcium oxide to sodium hydroxide is approximately 40:60.

* * * * *